United States Patent
Moen et al.

(10) Patent No.: US 8,795,717 B2
(45) Date of Patent: *Aug. 5, 2014

(54) TISSUE PRODUCTS INCLUDING A TEMPERATURE CHANGE COMPOSITION CONTAINING PHASE CHANGE COMPONENTS WITHIN A NON-INTERFERING MOLECULAR SCAFFOLD

(75) Inventors: Helen Kathleen Moen, Hortonville, WI (US); Jeffery Richard Seidling, Appleton, WI (US); Scott W. Wenzel, Neenah, WI (US); Corey Thomas Cunningham, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 801 days.

This patent is subject to a terminal disclaimer.

(21) Appl. No.: 12/622,571

(22) Filed: Nov. 20, 2009

(65) Prior Publication Data

US 2011/0124769 A1    May 26, 2011

(51) Int. Cl.
| | |
|---|---|
| *A61K 8/72* | (2006.01) |
| *A47K 10/16* | (2006.01) |
| *A61M 25/04* | (2006.01) |
| *D21H 27/00* | (2006.01) |

(52) U.S. Cl.
CPC ............... *A47K 10/16* (2013.01); *A61M 25/04* (2013.01); *D21H 27/002* (2013.01)
USPC ............. 424/443; 523/105; 424/402; 252/71; 252/73

(58) Field of Classification Search
CPC ...... A47K 10/16; A61M 25/04; D21H 27/002
USPC ................ 523/105; 424/443, 402; 252/71, 73
See application file for complete search history.

(56) References Cited

U.S. PATENT DOCUMENTS

| | | | |
|---|---|---|---|
| 1,253,603 A | 1/1918 | Keagy | |
| 1,579,124 A | 3/1926 | MacGrath | |
| 1,885,278 A | 11/1932 | Monett | |
| 2,721,554 A | 10/1955 | Joa | |

(Continued)

FOREIGN PATENT DOCUMENTS

| | | |
|---|---|---|
| BE | 0 905 997 A | 4/1987 |
| EP | 1 078 980 A1 | 2/2001 |

(Continued)

OTHER PUBLICATIONS

TAPPI Official Test Method T 411 om-89, "Thickness (Caliper) of Paper, Paperboard, and Combined Board," published by the TAPPI Press, Atlanta, Georgia, revised 1989, pp. 1-3.

(Continued)

*Primary Examiner* — Mark Kaucher
(74) *Attorney, Agent, or Firm* — Kimberly-Clark Worldwide, Inc.

(57) ABSTRACT

Wiping products, such as facial tissues, contain a temperature change composition that can provide a cooling sensation when contacted with the skin of a user. The temperature change composition includes a phase change material and a non-interfering molecular scaffold. The phase change materials, in one embodiment, can have a relatively high heat of fusion. When undergoing a phase change, the temperature change composition absorbs heat and thereby provides a cooling feeling or cooling sensation to the skin of a user.

15 Claims, 3 Drawing Sheets

(56) References Cited

U.S. PATENT DOCUMENTS

| | | |
|---|---|---|
| 3,264,172 A | 8/1966 | Regutti |
| 3,301,746 A | 1/1967 | Sanford et al. |
| 3,516,941 A | 6/1970 | Matson |
| 3,585,104 A | 6/1971 | Kleinert |
| 3,607,348 A | 9/1971 | Wray et al. |
| 3,812,000 A | 5/1974 | Salvucci, Jr. et al. |
| 3,974,025 A | 8/1976 | Ayers |
| 4,100,324 A | 7/1978 | Anderson et al. |
| 4,191,609 A | 3/1980 | Trokhan |
| 4,208,459 A | 6/1980 | Becker et al. |
| 4,379,143 A * | 4/1983 | Sherry et al. ............... 424/684 |
| 4,504,442 A | 3/1985 | Rosenblatt et al. |
| 4,514,345 A | 4/1985 | Johnson et al. |
| 4,528,239 A | 7/1985 | Trokhan |
| 4,585,482 A | 4/1986 | Tice et al. |
| 4,594,130 A | 6/1986 | Chang et al. |
| 4,604,313 A | 8/1986 | McFarland et al. |
| 4,637,859 A | 1/1987 | Trokhan |
| 4,793,898 A | 12/1988 | Laamanen et al. |
| 4,985,064 A | 1/1991 | Redlich et al. |
| 5,098,522 A | 3/1992 | Smurkoski et al. |
| 5,126,070 A | 6/1992 | Leifheit et al. |
| 5,275,700 A | 1/1994 | Trokhan |
| 5,328,565 A | 7/1994 | Rasch et al. |
| 5,350,624 A | 9/1994 | Georger et al. |
| 5,496,624 A | 3/1996 | Stelljes, Jr. et al. |
| 5,529,665 A | 6/1996 | Kaun |
| 5,554,467 A | 9/1996 | Trokhan et al. |
| 5,566,724 A | 10/1996 | Trokhan et al. |
| 5,595,628 A | 1/1997 | Gordon et al. |
| 5,628,876 A | 5/1997 | Ayers et al. |
| 5,840,671 A | 11/1998 | Fujimura et al. |
| 6,028,018 A | 2/2000 | Amundson et al. |
| 6,187,695 B1 | 2/2001 | Krzysik et al. |
| 6,258,249 B1 | 7/2001 | Simpson |
| 6,428,794 B1 | 8/2002 | Klofta et al. |
| 6,432,270 B1 | 8/2002 | Liu et al. |
| 6,582,558 B1 | 6/2003 | Liu |
| 6,749,860 B2 | 6/2004 | Tyrrell et al. |
| 6,825,393 B2 | 11/2004 | Roe et al. |
| 6,855,410 B2 | 2/2005 | Buckley |
| 6,860,967 B2 | 3/2005 | Baumoller et al. |
| 6,896,766 B2 | 5/2005 | Sarbo et al. |
| 6,949,167 B2 | 9/2005 | Shannon et al. |
| 7,005,557 B2 | 2/2006 | Klofta et al. |
| 7,008,507 B2 | 3/2006 | Urlaub et al. |
| 7,300,547 B2 | 11/2007 | Luu et al. |
| 7,361,361 B2 | 4/2008 | Luu et al. |
| 7,485,373 B2 | 2/2009 | Krzysik et al. |
| 7,582,577 B2 | 9/2009 | Vinson |
| 8,039,011 B2 * | 10/2011 | Flugge-Berendes et al. . 424/401 |
| 2002/0051823 A1 | 5/2002 | Yan et al. |
| 2002/0192552 A1 | 12/2002 | Lampe-Onnerud et al. |
| 2003/0077962 A1 | 4/2003 | Krzysik et al. |
| 2003/0108761 A1 | 6/2003 | Eddlemon |
| 2003/0133832 A1 | 7/2003 | D'Ottone |
| 2003/0147773 A1 | 8/2003 | Bryner et al. |
| 2003/0174810 A1 | 9/2003 | Korenev et al. |
| 2003/0188841 A1 | 10/2003 | Buder et al. |
| 2003/0230492 A1 | 12/2003 | Kadlec et al. |
| 2004/0009223 A1 | 1/2004 | Garg et al. |
| 2004/0076544 A1 | 4/2004 | Dao |
| 2004/0102125 A1 * | 5/2004 | Morman et al. ............... 442/394 |
| 2004/0140347 A1 | 7/2004 | Mihaylov et al. |
| 2004/0234561 A1 | 11/2004 | Ansmann et al. |
| 2005/0058674 A1 | 3/2005 | Joseph et al. |
| 2005/0058693 A1 | 3/2005 | Joseph et al. |
| 2005/0136765 A1 | 6/2005 | Shannon |
| 2005/0238701 A1 | 10/2005 | Kleinwaechter |
| 2005/0250402 A1 | 11/2005 | Wild et al. |
| 2005/0274470 A1 | 12/2005 | Shannon et al. |
| 2006/0029628 A1 * | 2/2006 | Kleinwaechter ............... 424/402 |
| 2006/0147502 A1 | 7/2006 | Koenig et al. |
| 2007/0145326 A1 * | 6/2007 | Joseph et al. ............... 252/70 |
| 2007/0148447 A1 | 6/2007 | Amundson et al. |
| 2007/0148448 A1 | 6/2007 | Joseph et al. |
| 2008/0045913 A1 | 2/2008 | Johnson et al. |
| 2008/0188560 A1 * | 8/2008 | Mohammadi et al. ........ 514/546 |
| 2009/0110656 A1 | 4/2009 | Lemke et al. |
| 2009/0155325 A1 | 6/2009 | Wenzel et al. |
| 2009/0297586 A1 * | 12/2009 | Shannon et al. ............... 424/443 |
| 2011/0123578 A1 | 5/2011 | Wenzel et al. |
| 2011/0123584 A1 | 5/2011 | Seidling et al. |
| 2011/0124769 A1 * | 5/2011 | Moen et al. ................... 523/105 |

FOREIGN PATENT DOCUMENTS

| | | |
|---|---|---|
| GB | 0 004 796 A | 7/1914 |
| GB | 0 016 501 A | 8/1916 |
| GB | 0 107 922 A | 7/1917 |
| JP | 63-296758 A | 12/1988 |
| JP | 06-154123 A | 6/1994 |
| JP | 09-276027 A | 10/1997 |
| JP | 2000-163629 A | 6/2000 |
| JP | 2001-043447 A | 2/2001 |
| JP | 2001-192306 A | 7/2001 |
| JP | 2006-042883 A | 2/2006 |
| KR | 10-2001-0108184 A | 12/2001 |
| WO | WO 99/42658 A1 | 8/1999 |
| WO | WO 00/66835 A1 | 11/2000 |
| WO | WO 01/00023 A1 | 1/2001 |
| WO | WO 03/035238 A2 | 5/2003 |

OTHER PUBLICATIONS

Avato, P. et al., "Allylsulfide Constituents of Garlic Volatile Oil As Antimicrobial Agents," *Phytomedicine*, vol. 7, No. 3, 2000, pp. 239-243.

Baysan, A. et al., "Antimicrobial Effect of a Novel Ozone-Generating Device On Micro-Organisms Associated With Primary Root Carious Lesions In Vitro," *Journal of the European Organisation for Caries Research (ORCA)*, vol. 34, No. 6, Nov.-Dec. 2000, pp. 498-501.

Cosentino, S. et al., "In-Vitro Antimicrobial Activity and Chemical Composition of Sardinian *Thymus* Essential Oils," *Letters in Applied Microbiology*, vol. 29(2), 1999, pp. 130-135.

Demirci, Fatih et al., "Antimicrobial Activities of *Ferulago* Essential Oils,"*Zeitschrift fur Naturforschung C*, vol. 55, No. 11-12, Nov.-Dec. 2000, pp. 886-889.

Djupesland, Per G. et al., "Nitric Oxide in the Nasal Airway: A New Dimension in Otorhinolaryngology," *American Journal of Otolaryngology—Head and Neck Medicine and Surgery*, vol. 22, No. 1, Jan.-Feb. 2001, pp. 19-32.

Ender, Peter, "Contaminated Currency: The True Return on the Dollar," Wright-Patterson AFB Medical Center, *101st General Meeting of the American Society for Microbiology*, Orlando, FL, May 20-24, 2001, Session 220/C, Paper C-332.

Flamini, Guido et al., "Antimicrobial Activity of the Essential Oil Of *Calamintha nepeta* and its Constituent Pilegone Against Bacteria and Fungi," *Phytotherapy Research*, vol. 13, No. 4, 1999, pp. 349-351.

Inoue, T. et al., "Solid-Liquid Phase Behavior Of Binary Fatty Acid Mixtures 3. Mixtures of Oleic Acid With Capric Acid (Decanoic Acid) and Caprylic Acid (Octanoic Acid)," Chemistry and Physics of Lipids, vol. 132, 2004, pp. 225-234.

Karatzas A.K. et al., "The Combined Action of Carvacrol and High Hydrostatic Pressure on *Listeria monocytogenes* Scott A," *Journal of Applied Microbiology*, vol. 90, No. 3, 2001, pp. 463-469.

Kulevanova, S. et al., "Investigation of Antimicrobial Activity of Essential Oils of Several Macedonian *Thymus* L. Species (Lamiaceae)," *Bollettino Chimico Farmaceutico*, vol. 139, No. 6, Nov.-Dec. 2000, pp. 276-280.

Liu, Wai-Kin et al., "Mechanisms of the Bactericidal Activity of Low Amperage Electric Current (DC)," *Journal of Antimicrobial Chemotherapy*, vol. 39, No. 6, 1997, pp. 687-695.

Marcinkiewicz, Janusz, "Nitric Oxide and Antimicrobial Activity of Reactive Oxygen Intermediates," *Immunopharmacology*, vol. 37, No. 1, Aug. 1997, pp. 35-41.

(56) References Cited

OTHER PUBLICATIONS

Messick, Chad R. et al., "In-Vitro Activity of Polyhexamethylene Biguanide (PHMB) Against Fungal Isolates Associated With Infective Keratitis," The Journal of Antimicrobial Chemotherapy, vol. 44, 1999, pp. 297-298.

Ruberto, Giuseppe et al. "Antioxidant and Antimicrobial Activity of *Foeniculum vulgare* and *Crithmum maritimum*, Essential Oils," *Planta Medica*, vol. 66, No. 8, Dec. 2000, pp. 687-693.

Smith, Anthony W. et al., "Nitric Oxide-Induced Potentiation of the Killing of *Burkholderia cepacia* by Reactive Oxygen Species: Implications for Cystic Fibrosis," *The Journal of Medical Microbiology*, vol. 48, No. 5, May 1999, pp. 419-423.

Wang, Hai-Hong et al., "Inhibition of *Escherichia coli* by Dimethyl Fumarate," *International Journal of Food Microbiology*, vol. 65, Nos. 1-2, 2001, pp. 125-130.

Webert, Kathryn E. et al., "Effects of Inhaled Nitric Oxide in a Rat Model of *Pseudomonas aeruginosa* Pneumonia," *Critical Care Medicine*, vol. 28, No. 7, Jul. 2000, pp. 2397-2405.

\* cited by examiner

TISSUE PRODUCTS INCLUDING A TEMPERATURE CHANGE COMPOSITION CONTAINING PHASE CHANGE COMPONENTS WITHIN A NON-INTERFERING MOLECULAR SCAFFOLD

BACKGROUND

Various healthcare and cosmetic products are applied to the skin in order to provide various benefits. Such products can include, for instance, lotions, creams, moisturizers, and the like. In some circumstances, the products are intended to provide a cooling feeling or cooling sensation to the skin once applied. Existing products typically provide skin cooling by combining skin cooling agents with other substances.

There are several different means to impart a cooling sensation to the skin, including using evaporation, neurosensory components, or thermodynamic agents such as phase change components. One example of a cooling agent is menthol which provides cooling in the form of a physiological or neurosensory effect on nerve endings in the human body that sense temperature. The cooling sensation from menthol is not due to latent heat of evaporation but appears to be the result of direct stimulus on the cold receptors at the nerve endings.

The use of phase change components to impart cooling is discussed, for instance, in PCT International Publication No. WO 2006/007564 entitled "Cosmetic Compositions and Methods for Sensory Cooling", which is incorporated herein by reference. In the '564 application, a skincare cosmetic composition is described in the form of a lotion that is intended for use in after-sun products, after-shave products, and body moisturizing products. The lotion is intended to create a cooling sensation on the skin by incorporating into the lotion components that absorb heat from the skin. In particular, ingredients are incorporated into the lotion that absorb heat from the skin and melt. The components have a relatively high heat of fusion which is defined in the '564 application as the heat absorbed by a unit of mass of a solid chemical element at its melting point in order to convert the solid into a liquid at the same temperature. The '564 application states that the relatively high heat of fusion facilitates the absorption of heat from the skin to aid in melting the solid ingredient when applied to the skin, thereby cooling the skin temperature. This approach is problematic since the skincare cosmetic composition directly contacts the skin and the phase change components can cause skin irritation.

The use of phase change agents to impart cooling in tissues is disclosed, for instance, in PCT Patent Application No. PCT/IB2009/051515 entitled "Tissue Products having a Cooling Sensation When Contacted with Skin", which is incorporated herein by reference. The '515 application discloses the use of a phase change agent between multiple layers of a dry tissue web with a separate hydrophobic lotion layer on the exterior surfaces of the tissue product to provide a cooling sensation. This approach is problematic since components of the hydrophobic lotion can migrate into the hydrophobic phase change agent and disrupt its ability to cool. Alternatively, the phase change agent can migrate into the lotion on the exterior of the tissue and can cause skin irritation.

In the above described products, the products are intended to be directly contacted with the skin. Therefore, a need exists for a means to effectively hold a phase change agent on or within a substrate, such as a tissue, such that it will cool the skin without allowing irritation to the skin. There also exists a need for a substrate, such as a tissue containing the composition, such that the composition can be delivered to the nose to moisturize, cool and soothe irritated noses, while holding this phase change agent within the substrate, keeping it from irritating skin.

SUMMARY

The present disclosure is generally directed to dry wiping products and particularly to dry substrates that, when held against the skin, can provide a cooling sensation. In one embodiment, for instance, the substrate can be a facial tissue. The facial tissue can be used to provide comfort to a user's nose. For example, when suffering from the common cold, a person's nose can become inflamed and sore. In one embodiment, the present disclosure is directed to a tissue product that can not only be used to wipe one's nose, but can also provide the nose with a cooling sensation giving comfort and relief.

The dry substrate may be a product that is made from at least one web of fibers, such as pulp fibers alone or in combination with synthetic fibers. A temperature change composition including a phase change component in combination with a non-interfering molecular scaffold is present on at least one side of the web. The phase change component undergoes a phase change at a temperature between about 20° C. and 32° C. within the dry tissue or similar dry wiping product for cooling the skin during use of the product.

The phase change agent incorporated into the temperature change composition can vary depending upon the particular application and the desired result. The phase change agent, for instance, can contain an oil soluble and hydrophobic material. Examples of phase change agents include hydrocarbons, waxes, oils, natural butters, fatty acids, fatty acid esters, dibasic acids, dibasic esters, 1-halides, primary alcohols, aromatic compounds, anhydrides, ethylene carbonates, polyhydric alcohols, and mixtures thereof. In one embodiment, for instance, a plurality of phase change agents can be incorporated into the temperature change composition. Particular examples of phase change agents well suited for use in the present disclosure include tricaprin, paraffin, nonadecane, octadecane, stearyl heptanoate, lauryl lactate, lauryl alcohol, capric acid, caprylic acid, cetyl babassuate, mangifera indica (mango) seed butter, theobroma cacao (cocoa) seed butter, butyrospermum parkii butter, Di-$C_{12-15}$ Alkyl Fumarate, stearyl caprylate, cetyl lactate, cetyl acetate, $C_{24-28}$ alkyl methicone, glyceryl dilaurate, stearamidopropyl PG-dimonium chloride phosphate, jojoba esters, and combinations thereof.

The phase change component may be present in an amount between about 1% by weight of the temperature change composition and about 99.9% by weight of the temperature change composition, more desirably between about 20% by weight of the temperature change composition and about 95% by weight of the temperature change composition, and even more desirably between about 50% by weight of the temperature change composition and about 90% by weight of the temperature change composition.

In an exemplary embodiment, the non-interfering molecular scaffold may be a crystalline diluent selected from fatty alcohols and fatty acids, the fatty alcohols and fatty acids having a chain length from 6 to about 60 carbon atoms, and more desirably having a chain length from 10 to about 30 carbon atoms. One suitable example of such fatty acids includes hydroxystearic acid.

In other embodiments, the non-interfering molecular scaffold is a polymer selected from polyethylene, poly $C_{10-30}$ alkyl acrylate, $C_{8-22}$ alkyl acrylates/methacrylic acid crosspolymer, $C_{8-22}$ alkyl acrylate/butyl dimethicone methacrylate copolymer, and mixtures thereof. In still other embodiments, the non-interfering molecular scaffold may be block copolymers selected from polystyrene-poly(ethylene-propylene) diblock copolymers, polystyrene-poly(ethylene-butylene)-polystyrene triblock copolymers, polystyrene-poly(ethylene-butylene-styrene)-polystyrene (S-EB/S-S) triblock copolymers, maleic anhydride-grafted polystyrene-poly(ethylene-butylene)-polystyrene triblock copolymers, maleic anhydride-grafted polystyrene-poly(ethylene-butylene-styrene)-polystyrene triblock copolymers, polystyrene-polybutadiene-poly(styrene-butadiene)-polybutadiene block copolymers, hydrogenated radial block copolymers, and mixtures thereof.

The non-interfering molecular scaffold may be present in an amount between about 1% by weight of the temperature change composition and about 50% by weight of the temperature change composition, more desirably between about 2% by weight of the temperature change composition and about 45% by weight of the temperature change composition, and even more desirably between about 5% by weight of the temperature change composition and about 40% by weight of the temperature change composition.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
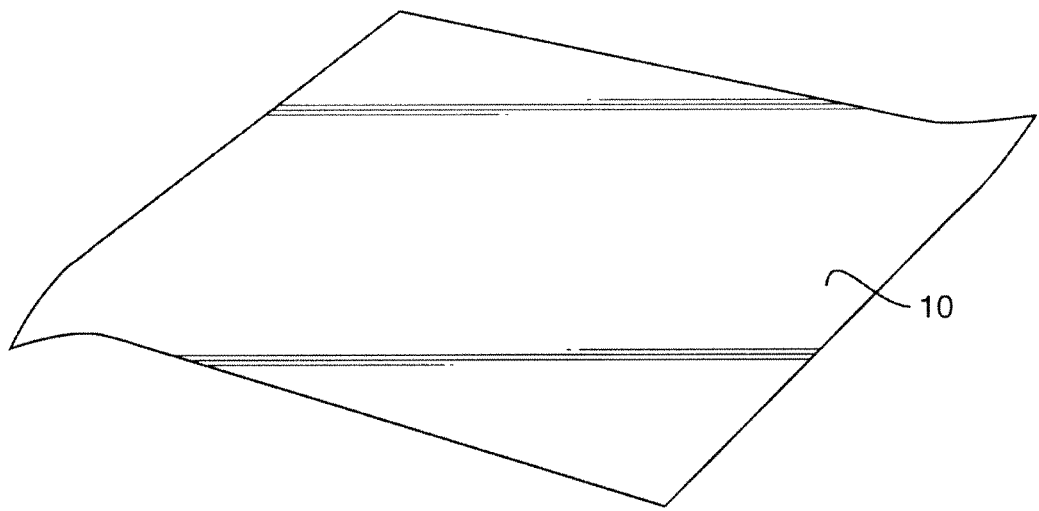
FIG. 1 is a perspective view of one embodiment of a wiping product made in accordance with the present disclosure.

Repeated use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

Dry, as used herein to describe tissue or wiping products, means that the product is supplied without any moisture beyond the equilibrium moisture that is generally associated with the product. The "equilibrium moisture" is the moisture that the sheet contains when exposed to ambient conditions for extended periods of time. The equilibrium moisture within the sheet will not change with time at the same relative humidity and temperature. The dry products will have equilibrium moisture contents typically of less than 15%, such as less than 10% such as from about 3% to about 8% under most ambient conditions that are encountered during routine use of the product.

The heat absorption factor, as used herein, expressed in $J/m^2$ is defined as the product of the heat of fusion of the cooling composition expressed in J/gram and the application rate of the cooling composition applied to the tissue product expressed in gsm.

Latent heat of fusion and melting points are determined by differential scanning calorimetry (DSC). Melting point, as herein defined, refers to the peak melt temperature as determined by DSC. Samples may be analyzed on a TA Instruments DSC 2920 Modulated DSC (Standard Cell) using the following experimental procedure: Approximately 5 mg of the respective material was weighed to the nearest 0.1 mg. Samples are run in the temperature interval from −50° C. to 100° C. with a heating/cooling rate of 10° C./min in an inert gas ($N_2$) atmosphere. The heat of fusion ($\Delta H_f$) is computed from the integral under the respective melting peak, with the reported results being the average value from 3 heating/cooling cycles.

The present disclosure is generally directed to dry wiping products, such as dry tissue products, that have improved perceived benefits. In particular, wiping products made in accordance with the present disclosure, when contacted against the skin, can provide a cooling sensation and feeling. The cooling sensation can, for instance, provide comfort and a soothing feeling to irritated skin. It is also found, that when used with a bath tissue, cooling can also evoke a sensation of wetness which can lead to a perception of improved cleaning. In one embodiment, the wiping product can be designed to provide a cooling sensation without having to transfer any chemical composition to the skin of the user.

In one embodiment, for instance, the present disclosure is directed to a dry wiping product, such as a facial tissue product, that contains a temperature change composition. The temperature change composition includes at least one phase change component that undergoes a phase change when elevated in temperature. The phase change component, for example, can have a relatively high heat of fusion which allows it to absorb great amounts of thermal energy and to regulate to a lower temperature than the environment. In particular, when the wiping product is heated such as being contacted with one's skin, the phase change component quickly warms to its melting point. Due to the high heat of fusion, significant amounts of heat can then be absorbed without temperature change until the phase change component is completely melted. In turn, a cooling sensation is provided to the skin of the user.

Referring to FIG. 1, one embodiment of a tissue product 10 made in accordance with the present disclosure is shown. The tissue product 10 can contain any suitable base sheet made from various different types of fiber furnishes. The tissue product 10 can also be a single ply product or can contain multiple tissue webs laminated together.

Tissue webs that may be used to construct the tissue product 10, for instance, can generally contain pulp fibers either alone or in combination with other fibers. Each tissue web can generally have a bulk density of at least 2 cc/g, such as at least 3 cc/g.

Fibers suitable for making tissue webs contain any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898 issued Dec. 27, 1988 to Laamanen et al.; U.S. Pat. No. 4,594,130 issued Jun. 10, 1986 to Chang et al.; and U.S. Pat. No. 3,585,104 issued Jun. 15, 1971 to Kleinert. Useful fibers can also be produced by anthraquinone pulping, exemplified by U.S. Pat. No. 5,595,628 issued Jan. 21, 1997 to Gordon et al.

A portion of the fibers, such as up to 50% or less by dry weight, or from about 5% to about 30% by dry weight, can be synthetic fibers such as rayon, polyolefin fibers, polyester fibers, bicomponent sheath-core fibers, multi-component binder fibers, and the like. An exemplary polyethylene fiber is Pulpex®, available from Hercules, Inc. (Wilmington, Del.). Any known bleaching method can be used. Synthetic cellulose fiber types include rayon in all its varieties and other fibers derived from viscose or chemically-modified cellulose. Chemically treated natural cellulosic fibers can be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

Other papermaking fibers that can be used in the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a tissue web can also be utilized in the present disclosure. For example, a papermaking process of the present disclosure can utilize creping, wet creping, double creping, embossing, wet pressing, air pressing, through-air drying, creped through-air drying, uncreped through-air drying, hydroentangling, air laying, as well as other steps known in the art.

The tissue web may be formed from a fiber furnish containing pulp fibers in an amount of at least about 50% by weight, such as at least about 60% by weight, such as at least about 70% by weight, such as at least about 80% by weight, such as at least about 90% by weight, such as 100% by weight.

Also suitable for products of the present disclosure are tissue sheets that are pattern densified or imprinted, such as the tissue sheets disclosed in any of the following U.S. Pat. No. 4,514,345 issued on Apr. 30, 1985 to Johnson et al.; U.S. Pat. No. 4,528,239 issued on Jul. 9, 1985 to Trokhan; U.S. Pat. No. 5,098,522 issued on Mar. 24, 1992 to Smurkoski et al.; U.S. Pat. No. 5,260,171 issued on Nov. 9, 1993 to Smurkoski et al.; U.S. Pat. No. 5,275,700 issued on Jan. 4, 1994 to Trokhan; U.S. Pat. No. 5,328,565 issued on Jul. 12, 1994 to Rasch et al.; U.S. Pat. No. 5,334,289 issued on Aug. 2, 1994 to Trokhan et al.; U.S. Pat. No. 5,431,786 issued on Jul. 11, 1995 to Rasch et al.; U.S. Pat. No. 5,496,624 issued on Mar. 5, 1996 to Steltjes, Jr. et al.; U.S. Pat. No. 5,500,277 issued on Mar. 19, 1996 to Trokhan et al.; U.S. Pat. No. 5,514,523 issued on May 7, 1996 to Trokhan et al.; U.S. Pat. No. 5,554,467 issued on Sep. 10, 1996 to Trokhan et al.; U.S. Pat. No. 5,566,724 issued on Oct. 22, 1996 to Trokhan et al.; U.S. Pat. No. 5,624,790 issued on Apr. 29, 1997 to Trokhan et al.; and U.S. Pat. No. 5,628,876 issued on May 13, 1997 to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

The tissue web can also be formed without a substantial amount of inner fiber-to-fiber bond strength. In this regard, the fiber furnish used to form the base web can be treated with a chemical debonding agent. The debonding agent can be added to the fiber slurry during the pulping process or can be added directly to the headbox. Suitable debonding agents that may be used in the present disclosure include cationic debonding agents such as fatty dialkyl quaternary amine salts, mono fatty alkyl tertiary amine salts, primary amine salts, imidazoline quaternary salts, silicone quaternary salt and unsaturated fatty alkyl amine salts. Other suitable debonding agents are disclosed in U.S. Pat. No. 5,529,665 issued on Jun. 25, 1996 to Kaun which is incorporated herein by reference. In particular, Kaun '665 discloses the use of cationic silicone compositions as debonding agents.

In one embodiment, the debonding agent used in the process of the present disclosure is an organic quaternary ammonium chloride and, particularly, a silicone-based amine salt of a quaternary ammonium chloride. For example, the debonding agent can be PROSOFT® TQ1003, marketed by the Hercules Corporation. The debonding agent can be added to the fiber slurry in an amount from about 1 kg per metric tonne to about 10 kg per metric tonne of fibers present within the slurry.

In an alternative embodiment, the debonding agent can be an imidazoline-based agent. The imidazoline-based debonding agent can be obtained, for instance, from the Witco Corporation (Greenwich, Conn.). The imidazoline-based debonding agent can be added in an amount of between 2 kg per metric tonne to about 15 kg per metric tonne.

In one embodiment, the debonding agent can be added to the fiber furnish according to a process as disclosed in PCT Application having an International Publication No. WO 99/34057 filed on Dec. 17, 1998 or in PCT Published Application having an International Publication No. WO 00/66835 filed on Apr. 28, 2000, which are both incorporated herein by reference. In the above publications, a process is disclosed in which a chemical additive, such as a debonding agent, is adsorbed onto cellulosic papermaking fibers at high levels. The process includes the steps of treating a fiber slurry with an excess of the chemical additive, allowing sufficient residence time for adsorption to occur, filtering the slurry to remove unadsorbed chemical additives, and redispersing the filtered pulp with fresh water prior to form a nonwoven web.

Optional chemical additives may also be added to the aqueous papermaking furnish or to the formed embryonic web to impart additional benefits to the product and process and are not antagonistic to the intended benefits of the dry substrate. The following materials are included as examples of additional chemicals that may be applied to the web along with the additive composition. The chemicals are included as examples and are not intended to limit the scope of the invention. Such chemicals may be added at any point in the papermaking process, including being added simultaneously with the additive composition in the pulp making process, wherein said additive or additives are blended directly with the additive composition.

Additional types of chemicals that may be added to the paper web include, but are not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin E, silicone, lotions in general, and the like, may also be incorporated into the finished products.

In general, the products can be used in conjunction with any known materials and chemicals that are not antagonistic to its intended use. Examples of such materials include, but are not limited to, odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients, and the like.

Tissue webs that may be treated in accordance with the present disclosure may include a single homogenous layer of fibers or may include a stratified or layered construction. For instance, the tissue web ply may include two or three layers of fibers. Each layer may have a different fiber composition.

Each of the fiber layers contains a dilute aqueous suspension of papermaking fibers. The particular fibers contained in each layer generally depends upon the product being formed and the desired results. In one embodiment, for instance, a middle layer contains southern softwood kraft fibers either alone or in combination with other fibers, such as high yield fibers. The outer layers, on the other hand, can contain softwood fibers, such as northern softwood kraft.

In an alternative embodiment, the middle layer may contain softwood fibers for strength, while the outer layers may contain hardwood fibers, such as eucalyptus fibers, for a perceived softness.

The basis weight of tissue webs made in accordance with the present disclosure can vary depending upon the final product. For example, the process may be used to produce facial tissues, bath tissues, paper towels, industrial wipers, and the like. In general, the basis weight of the tissue products may vary from about 10 gsm to about 80 gsm, such as from about 20 gsm to about 60 gsm. For bath and facial tissues, for instance, the basis weight may range from about 10 gsm to about 60 gsm. For paper towels, on the other hand, the basis weight may range from about 25 gsm to about 80 gsm.

The tissue web bulk may also vary from about 2 cc/g to 20 cc/g, such as from about 5 cc/g to 15 cc/g. The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc. (Newberg, Oreg.). The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

In multiple ply products, the basis weight of each tissue web present in the product can also vary. In general, the total basis weight of a multiple ply product will generally be the same as indicated above, such as from about 20 gsm to about 80 gsm. Thus, the basis weight of each ply can be from about 5 gsm to about 60 gsm, such as from about 10 gsm to about 40 gsm.

In accordance with the present disclosure, the tissue product 10 contains a temperature change composition for imparting a cooling sensation to the skin of a user. To achieve delivery of the cooling sensation, a temperature change composition including a non-interfering molecular scaffold and a phase change component incorporated within the non-interfering molecular scaffold.

The temperature change composition includes at least one phase change component that undergoes a phase change when heated which, in turn, provides a cooling sensation to the skin. The temperature change composition can be incorporated into the tissue product 10 using any suitable method or technique. For example, the temperature change composition can be sprayed onto the tissue product, extruded onto the tissue product, or printed onto the tissue product using, for instance, flexographic printing, direct gravure printing, or indirect gravure printing. In still another embodiment, the temperature change composition can be applied to the tissue product using any suitable coating equipment, such as a knife coater or slot coater. As the temperature change composition is solid at room temperature in one embodiment, it may be desirable to melt the composition prior to application to the tissue web. The application of such molten materials to a finished tissue web is well known in the art. At times it may also be advantageous to cool the web directly after application of the molten phase change component, especially when the treated product is wound into a spirally wound roll either for a finished product or for further processing. The cooling of the web below the melting point of the phase change component reduces the potential of the spirally wound web from becoming "blocked". "Blocked" as used herein refers to the tendency of adjacent facing sheets in the spirally wound roll to adhere to each other and restrict the ability to unwind the web from the spirally wound roll.

In general, a phase change component includes any substance that has the capability of absorbing or releasing thermal energy to reduce or eliminate heat flow at or within a temperature stabilizing range. The temperature stabilizing range may include a particular transition temperature or range of transition temperatures. A phase change component used in conjunction with various aspects of the present disclosure preferably will be capable of altering a flow of thermal energy during a time when the phase change component is absorbing or releasing heat, typically as the phase change component undergoes a transition between two states (e.g., liquid and solid states, liquid and gaseous states, solid and gaseous states, or two solid states). This action is typically transient, meaning it will occur until a latent heat of the phase change component is absorbed or released during a heating or cooling process. Thermal energy may be stored or removed from the phase change component, and the phase change component typically can be effectively recharged by a source of heat or cold. For the purposes of the present disclosure, the temperature change compositions exhibit a phase change at temperatures between about 23° C. and about 35° C. such as to be appropriate for use in cooling skin. In other embodiments of the present disclosure, materials may be chosen with transition temperatures between about 23° C. and about 32° C., between about 26° C. and about 32° C., or within any other suitable range. The phase change temperature is selected such that the phase change occurs between the ambient temperature of the product and the external temperature of the user's skin.

The temperature change composition of the present disclosure may contain a mixture of phase change components that have a mixture of transition temperatures. When a mixture of phase change components is used, the components can be selected so as to have a collective melting point within the above mentioned limits. In some cases, the melting points of the individual phase change components containing the temperature change composition may lie outside the melting point limits for the phase change temperature of the temperature change composition. However, the mixture of phase change components will display a phase change within the desired temperature limits. When the temperature change composition is held against the skin either directly or indirectly, the composition warms to the temperature of the skin from room temperature. The phase change component then melts at its specified phase change temperature. That melting requires heat, which is taken from the skin, imparting a feeling of cooling. Once the material is melted, the cooling sensation dissipates. Having a range of phase change temperatures (melting points in this case) of the phase change components may extend the range of temperatures where cooling is felt. In one example, a combination of phase change components having phase change temperatures at 18° C., 28° C., and 35° C. are combined to create a temperature change composition having a melting point between 23° C. and 32° C.

Suitable phase change components include, by way of example and not by limitation, encapsulated phase change powder, (e.g., LURAPRET, a purified, encapsulated paraffin available from BASF and MPCM 43-D available from Microtek Laboratories), hydrocarbons (e.g., straight chain alkanes or paraffinic hydrocarbons, branched-chain alkanes, unsaturated hydrocarbons, halogenated hydrocarbons, and alicyclic hydrocarbons), waxes, natural butters, fatty acids, fatty acid esters, dibasic acids, dibasic esters, 1-halides, primary alcohols, aromatic compounds, anhydrides (e.g., stearic anhydride), ethylene carbonate, polyhydric alcohols (e.g., 2,2-dimethyl-1,3-propanediol, 2-hydroxymethyl-2-methyl-1,3-propanediol, pentaerythritol, dipentaerythritol, pentaglycerine, tetramethylol ethane, neopentyl glycol, tetramethylol propane, monoaminopentaerythritol, diaminopentaerythritol, 1,2,3-propanol tridecanoate, and tris(hydroxymethyl)acetic acid), polymers (e.g., polyethylene, polyethylene glycol, polypropylene, polypropylene glycol, polytetramethylene glycol, and copolymers, such as polyacrylate or poly(meth)acrylate with alkyl hydrocarbon side chain or with polyethylene glycol side chain and copolymers containing polyethylene, polyethylene glycol, polypropylene, polypropylene glycol, or polytetramethylene glycol), and mixtures thereof. Well suited phase change components are tricaprin, paraffin, nonadecane, octadecane, stearyl heptanoate, lauryl lactate, lauryl alcohol, capric acid, caprylic acid, cetyl babassuate, mangifera indica (mango) seed butter, theobroma cacao (cocoa) seed butter, butyrospermum parkii butter, Di-$C_{12-15}$ Alkyl Fumarate, stearyl caprylate, cetyl lactate, cetyl acetate, $C_{24-28}$ alkyl methicone, glyceryl dilaurate, stearamidopropyl PG-dimonium chloride phosphate, jojoba esters, and combinations thereof.

As described above, in one embodiment, the temperature change composition may contain a mixture of two or more phase change components. In one particular embodiment, the temperature change composition contains a mixture of stearyl heptanoate and n-octadecane.

Phase change components of the present disclosure may include phase change components in a non-encapsulated form and phase change components in an encapsulated form. A phase change component in a non-encapsulated form may be provided as a solid in a variety of forms (e.g., bulk form, powders, pellets, granules, flakes, paste and so forth) or as a liquid in a variety of forms (e.g., molten form, and so forth).

Another aspect of the temperature change compositions is the heat of fusion of the temperature change composition containing the phase change components. The temperature change compositions of the present disclosure can have heats of fusion of at least about 100 J/g. For instance, in one embodiment, the temperature change composition contains a hydrocarbon as the phase change component, such as a straight chain hydrocarbon. The hydrocarbon, for instance, may contain more than about 10 carbon atoms in the chain, such as from about 10 carbon atoms to about 30 carbon atoms in the chain. Particular examples of phase change components include, for instance, octadecane (heat of fusion of about 213 J/g), nonadecane, stearyl heptanoate, and mixtures thereof.

The phase change components can be contained in the temperature change composition in an amount from about 1% by weight to 99% by weight, such as from about 5% by weight to about 95% by weight. For example, in particular embodiments, the phase change components may be present in the temperature change composition in an amount from about 10% by weight to about 90% by weight.

As discussed above, the temperature change composition includes a non-interfering molecular scaffold. The non-interfering molecular scaffold is defined as any ingredient that can be combined with the phase change component such that a homogeneous mixture can be obtained and the mixture maintains a gel-like consistency above skin temperature (approximately 40° C.). Additionally, the non-interfering molecular scaffold is defined as any ingredient that can be combined with the phase change component such that the mixture retains at least 75% of the enthalpy of the pure phase change component. Not to be held to any one theory, but it is believed that the non-interfering molecular scaffold creates a network for the phase change component to aggregate within and around such that the crystal size of the phase change component is large enough to provide an effective cooling sensation compared to the pure phase change material. Unexpectedly, the smaller amount of phase change component allows effective cooling, but the phase change component is maintained within the non-interfering molecular scaffold such that the phase change component does not penetrate the skin or cause irritation, or redistribute within the tissue.

Use of a non-interfering molecular scaffold helps to prevent the phase change agents from substantially contacting the skin and/or transferring to the skin and causing irritation or being removed from the product prior to use, especially when molten. Thus, the non-interfering molecular scaffold can reduce irritation and prevent removal of the phase change agents from the product prior to use. With prior temperature change compositions, disclosed in for example, PCT Patent Application No. PCT/IB2009/051515 entitled "Tissue Products having a Cooling Sensation When Contacted with Skin," the phase change materials transfer to the skin and cause irritation.

Additionally, the non-interfering molecular scaffold may be thermally reversible. Having a thermally reversible composition allows the product to be exposed to extreme temperatures during transportation of the product and still work effectively in the home when used by a consumer. The thermally reversible temperature change composition disclosed herein will change from a solid state to liquid state and back to a solid as the temperatures change. Thus, the phase change materials to provide a cooling effect are still available after long periods of storage and transportation at various temperatures. Previous temperature change composition, disclosed in for example, PCT Patent Application No. PCT/IB2009/051515 are not thermally reversible and do not provide these benefits.

In an exemplary embodiment, the non-interfering molecular scaffold may include a crystalline diluent selected from fatty alcohols and fatty acids. Exemplary fatty alcohols and fatty acids for use as the crystalline diluents have a carbon chain length from about 6 to 60 carbons, more desirably having a carbon chain length from about 8 to 40 carbons and even more desirably having a carbon chain length of from about 10 to 30 carbons.

In another embodiment, the non-interfering molecular scaffold may include a polymer. Desirably, the non-interfering molecular scaffold could include, but not be limited to polymers, such as polyethylene, poly $C_{10-30}$ alkyl acrylate, $C_{8-22}$ alkyl acrylates/methacrylic acid crosspolymer, $C_{8-22}$ Alkyl acrylate/butyl dimethicone methacrylate copolymer. One particularly desirable non-interfering molecular scaffold is the polyethylene, Asensa PR200, commercially available from Honeywell.

Additionally, the non-interfering molecular scaffold could include, but is not limited to, block copolymers. Methods of preparing block copolymers are known in the art and many hydrogenated block copolymers are commercially available. Illustrative commercially available hydrogenated block copolymers include the polystyrene-poly(ethylene-propylene) diblock copolymers available from Kraton Polymers as Kraton G1701 and G1702; the polystyrene-poly(ethylene-butylene)-polystyrene triblock copolymers available from Kraton Polymers as Kraton G1641, G1650, G1651, G1654, G1657, G1726, G4609, G4610, GRP-6598, RP-6924, MD-6932M, MD-6933, and MD-6939; the polystyrene-poly(ethylene-butylene-styrene)-polystyrene (S-EB/S-S) triblock copolymers available from Kraton Polymers as Kraton RP-6935 and RP-6936, the polystyrene-poly(ethylene-propylene)-polystyrene triblock copolymers available from Kraton Polymers as Kraton G1730; the maleic anhydride-grafted polystyrene-poly(ethylene-butylene)-polystyrene triblock copolymers available from Kraton Polymers as Kraton G1901, G1924, and MD-6684; the maleic anhydride-grafted polystyrene-poly(ethylene-butylene-styrene)-polystyrene triblock copolymer available from Kraton Polymers as Kraton MD-6670; the polystyrene-poly(ethylene-butylene)-polystyrene triblock copolymer containing 67 weight percent polystyrene available from Asahi Kasei Elastomer as TUFTEC H1043; the polystyrene-poly(ethylene-butylene)-polystyrene triblock copolymer containing 42 weight percent polystyrene available from Asahi Kasei Elastomer as TUFTEC H1051; the polystyrene-poly(butadiene-butylene)-polystyrene triblock copolymers available from Asahi Kasei Elastomer as TUFTEC P1000 and P2000; the polystyrene-polybutadiene-poly(styrene-butadiene)-polybutadiene block copolymer available from Asahi Kasei Elastomer as S.O.E.-SS L601; the hydrogenated radial block copolymers available from Chevron Phillips Chemical Company as K-Resin KK38, KR01, KR03 and KR05; the polystyrene-poly(ethylene-butylene)-polystyrene triblock copolymer containing about 60 weight percent polystyrene available from Kuraray as SEPTON S8104; the polystyrene-poly(ethylene-ethylene/propylene)-polystyrene triblock copolymers available from Kuraray as SEPTON S4044, S4055, S4077, and S4099; and the polystyrene-poly(ethylene-propylene)-polystyrene triblock copolymer containing about 65 weight percent polystyrene available from Kuraray as SEPTON S2104. One particular preferred block copolymer is Kraton RP-6935 and RP-6936 from Kraton Polymers. Mixtures of two of more block copolymers may also be used as the non-interfering molecular scaffold.

In addition, the non-interfering molecular scaffold may be selected from combinations of the crystalline diluents, polymers, and block copolymers described above. For example, one desirable non-interfering molecular scaffold may include both stearyl alcohol and polyethylene.

Typically, the temperature change compositions contain a non-interfering molecular scaffold in an amount from about 1% by weight of the temperature change composition to about 50% by weight of the temperature change composition, more typically from about 2% by weight of the temperature change composition to about 45% by weight of the temperature change composition, and more typically from about 5% by weight of the temperature change composition to about 40% by weight of the temperature change composition.

Perhaps more importantly, however, is the heat absorption factor of the products. The heat absorption factor, expressed in $J/m^2$, is the product of the heat of fusion of the temperature change composition expressed in J/gram and the application rate of the temperature change composition applied to the tissue product expressed in gsm. The heat absorption factor of the products can be at least about 500 $J/m^2$, such as at least about 1000 $J/m^2$ such as from about 1000 $J/m^2$ to about 4000 $J/m^2$ or greater. For many applications, the temperature change composition can be applied to a tissue web such that the phase change components are present on the web in an amount from about 4 gsm to about 40 gsm.

In addition to one or more phase change components, the temperature change composition can contain various other ingredients and components. Examples of other ingredients that may be included within the temperature change composition are emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, anti-wrinkle actives, soothing agents, antioxidants, and the like.

Thus, the temperature change compositions may further optionally include one or more emollients, which typically act to soften, soothe, and otherwise lubricate and/or moisturize the skin. Suitable emollients that can be incorporated into the compositions include oils such as natural oils such as jojoba, sunflower, safflower, and the like, synthetic based oils such as, petrolatum, mineral oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, glycerol esters and derivatives, propylene glycol esters and derivatives, fatty acid esters and derivatives, alkoxylated carboxylic acids, alkoxylated alcohols, and combinations thereof.

Ethers such as eucalyptol, cetearyl glucoside, dimethyl isosorbic polyglyceryl-3 cetyl ether, polyglyceryl-3 decyltetradecanol, propylene glycol myristyl ether, and combinations thereof, can also suitably be used as emollients.

The temperature change composition may include one or more emollients in an amount from about 0.01% by weight of the temperature change composition to about 70% by weight of the temperature change composition, more desirably from about 0.05% by weight of the temperature change composition to about 50% by weight of the temperature change composition, and even more desirably from about 0.1% by weight of the temperature change composition to about 40% by weight of the temperature change composition.

The temperature change composition may include one or more viscosity enhancers in an amount from about 0.01% by weight of the temperature change composition to about 25% by weight of the temperature change composition, more desirably from about 0.05% by weight of the temperature change composition to about 10% by weight of the temperature change composition, and even more desirably from about 0.1% by weight of the temperature change composition to about 10% by weight of the temperature change composition.

The temperature change composition may optionally further contain rheology modifiers. Rheology modifiers may help increase the melt point viscosity of the composition so that the composition readily remains on the surface of a personal care product.

The temperature change composition may optionally further contain humectants. Examples of suitable humectants include glycerin, glycerin derivatives, 1,3 propanediol, sodium hyaluronate, betaine, amino acids, glycosaminoglycans, honey, sugar alcohols, sorbitol, glycols, polyols, sugars, hydrogenated starch hydrolysates, salts of PCA, lactic acid, lactates, and urea. A particularly preferred humectant is glycerin. The temperature change composition may suitably include one or more humectants in an amount from about 0.05% by weight of the temperature change composition to about 25% by weight of the temperature change composition.

The temperature change composition may optionally further contain film formers. Examples of suitable film formers include lanolin derivatives (e.g., acetylated lanolins), superfatted oils, cyclomethicone, cyclopentasiloxane, dimethicone, synthetic and biological polymers, proteins, quaternary ammonium materials, starches, gums, cellulosics, polysaccharides, albumen, acrylates derivatives, IPDI derivatives, and the like. The temperature change composition may suitably include one or more film formers in an amount from about 0.01% by weight of the temperature change composition to about 20% by weight of the temperature change composition.

The temperature change composition may optionally further contain slip modifiers. Examples of suitable slip modifiers include bismuth oxychloride, iron oxide, mica, surface treated mica, ZnO, $ZrO_2$, silica, silica silyate, colloidal silica, attapulgite, sepiolite, starches (i.e. corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, aluminum oxide, silicone resin, barium sulfate, calcium carbonate, cellulose acetate, polymethyl methacrylate, polymethylsilsequioxane, talc, tetrafluoroethylene, silk powder, boron nitride, lauroyl lysine, synthetic oils, natural oils, esters, silicones, glycols, and the like. The temperature change composition may suitably include one or more slip modifiers in an amount from about 0.01% by weight of the temperature change composition to about 20% by weight of the temperature change composition.

The temperature change composition may also further contain surface modifiers. Examples of suitable surface modifiers include silicones, quaternium materials, powders, salts, peptides, polymers, clays, and glyceryl esters. The temperature change composition may suitably include one or more surface modifiers in an amount from about 0.01% by weight of the temperature change composition to about 20% by weight of the temperature change composition.

The temperature change composition may also further contain skin protectants. Examples of suitable skin protectants include ingredients referenced in SP Monograph (21 CFR part 347). Suitable skin protectants and amounts include those set forth in SP Monograph, Subpart B—Active Ingredients Sec 347.10: (a) Allantoin, 0.5 to 2%, (b) Aluminum hydroxide gel, 0.15 to 5%, (c) Calamine, 1 to 25%, (d) Cocoa butter, 50 to 100%, (e) Cod liver oil, 5 to 13.56%, in accordance with 347.20(a)(1) or (a)(2), provided the product is labeled so that the quantity used in a 24-hour period does not exceed 10,000 U.S.P. Units vitamin A and 400 U.S.P. Units cholecalciferol, (f) Colloidal oatmeal, 0.007% minimum; 0.003% minimum in combination with mineral oil in accordance with §347.20(a)(4), (g) Dimethicone, 1 to 30%, (h) Glycerin, 20 to 45%, (i) Hard fat, 50 to 100%, (j) Kaolin, 4 to 20%, (k) Lanolin, 12.5 to 50%, (l) Mineral oil, 50 to 100%; 30 to 35% in combination with colloidal oatmeal in accordance with §347.20(a)(4), (m) Petrolatum, 30 to 100%, (n) Sodium bicarbonate, (o) Topical starch, 10 to 98%, (p) White petrolatum, 30 to 100%, (q) Zinc acetate, 0.1 to 2%, (r) Zinc carbonate, 0.2 to 2%, (s) Zinc oxide, 1 to 25%.

The temperature change composition may also further contain quaternary ammonium materials. Examples of suitable quaternary ammonium materials include polyquaternium-7, polyquaternium-10, benzalkonium chloride, behentrimonium methosulfate, cetrimonium chloride, cocamidopropyl pg-dimonium chloride, guar hydroxypropyltrimonium chloride, isostearamidopropyl morpholine lactate, polyquaternium-33, polyquaternium-60, polyquaternium-79, quaternium-18 hectorite, quaternium-79 hydrolyzed silk, quaternium-79 hydrolyzed soy protein, rapeseed amidopropyl ethyldimonium ethosulfate, silicone quaternium-7, stearalkonium chloride, palmitamidopropyltrimonium chloride, butylglucosides, hydroxypropyltrimonium chloride, laurdimoniumhydroxypropyl decylglucosides chloride, and the like. The temperature change composition may suitably include one or more quaternary materials in an amount from about 0.01% by weight of the temperature change composition to about 20% by weight of the temperature change composition.

The temperature change composition may also further contain additional emulsifiers. As mentioned above, the natural fatty acids, esters and alcohols and their derivatives, and combinations thereof, may act as emulsifiers in the composition. Optionally, the composition may contain an additional emulsifier other than the natural fatty acids, esters and alcohols and their derivatives, and combinations thereof. Examples of suitable emulsifiers include nonionics such as polysorbate 20, polysorbate 80, anionics such as DEA phosphate, cationics such as behentrimonium methosulfate, and the like. The temperature change composition may suitably include one or more additional emulsifiers in an amount from about 0.01% by weight of the temperature change composition to about 20% by weight of the temperature change composition.

The temperature change composition may additionally include adjunct components conventionally found in pharmaceutical compositions in their art-established fashion and at their art-established levels. For example, the compositions may contain additional compatible pharmaceutically active materials for combination therapy, such as antimicrobials, antioxidants, anti-parasitic agents, antipruritics, antifungals, antiseptic actives, biological actives, astringents, keratolytic actives, local anesthetics, anti-stinging agents, anti-reddening agents, skin soothing agents, and combinations thereof. Other suitable additives that may be included in the temperature change compositions include colorants, deodorants, fragrances, perfumes, emulsifiers, anti-foaming agents, lubricants, natural moisturizing agents, skin conditioning agents, skin protectants and other skin benefit agents (e.g., extracts such as aloe vera and anti-aging agents such as peptides), solvents, solubilizing agents, suspending agents, wetting agents, humectants, preservatives, pH adjusters, buffering agents, dyes and/or pigments, and combinations thereof.

Although the temperature change composition can be present on an exterior surface of the tissue product 10 as shown on FIG. 1, in one embodiment, the temperature change composition can be incorporated into the tissue product in a manner so that substantially none of the temperature change composition is present on the exterior surfaces. For instance, referring to FIG. 2, a tissue product 20 is shown that is comprised of a first tissue web 22 laminated to a second tissue web 24. As shown, positioned in between the first tissue web 22 and the second tissue web 24 is a temperature change composition 26. By locating the temperature change composition 26 in between the tissue webs, the temperature change composition is substantially prevented from being transferred to a user's skin. When the tissue product 20, however, is held against the skin, body heat will be absorbed by the temperature change composition 26 through the tissue webs thus elevating in temperature. The increase in temperature will cause a phase change to occur in the phase change component providing a cooling sensation to the skin of the user.

In one specific embodiment the cooling tissue product is a facial tissue containing three or more plies, two outer plies and one or more interior plies. The temperature change composition is applied to at least one of the one or more interior plies. In another embodiment, the cooling tissue product is a facial tissue containing two plies, containing two outer facing surfaces and two oppositely facing inner surfaces. The phase change composition is applied to one or both of the oppositely facing inner surfaces. In another embodiment, the product is a multi-ply tissue product where the phase change composition is applied selectively to the inner portion of the multi-ply product so as to minimize blocking.

In this manner, other beneficial compositions may be applied to the exterior surface of the tissue product and used in conjunction with the temperature change composition 26. For example, in one embodiment, a lotion that is intended to moisturize the skin can be present on at least one exterior surface of the tissue product and may work in conjunction with the temperature change composition. In this manner, the tissue product 20 can not only provide a cooling sensation to the user, but can also transfer a moisturizer to the skin.

In addition to lotions, any other suitable composition may also be applied to the exterior surface. For instance, in one embodiment, various softening agents may be present on the exterior surfaces of the tissue product. One example of a softening agent may contain a polysiloxane.

Figure 2:
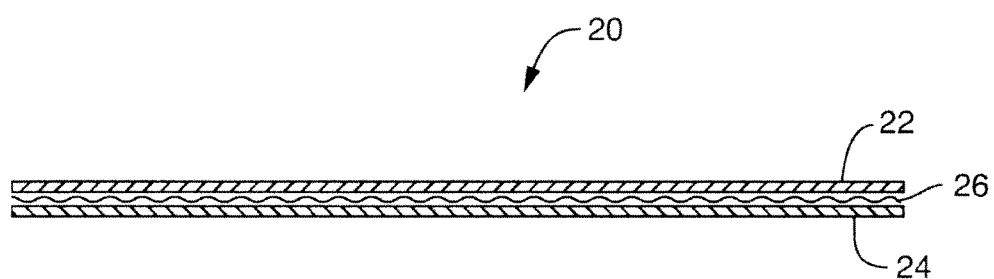
FIG. 2 is a cross-sectional view of the wiping product illustrated in FIG. 1.
Figure 3:
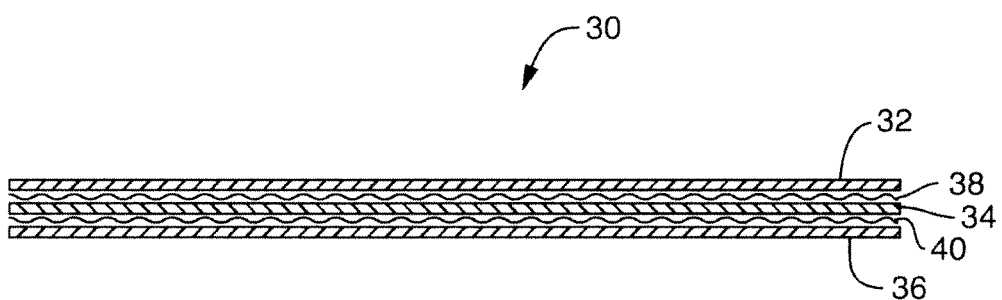
FIG. 3 is a cross-sectional view of another embodiment of a wiping product made in accordance with the present disclosure.

In addition to a 2-ply product as shown in FIG. 2, other tissue products may be made that can include more than two plies. For example, a 3-ply tissue product 30 is illustrated in FIG. 3. As shown, the tissue product 30 includes a middle tissue web 34 laminated to outer tissue webs 32 and 36. In accordance with the present disclosure, a temperature change composition is located in between the first tissue web 32 and the middle tissue web 34. A temperature change composition 40 is also positioned in between the middle tissue web 34 and the second outer tissue web 36.

In an alternative embodiment, the temperature change composition can also be present on one or more exterior surfaces of a tissue product. For instance, referring to FIG. 4, in one embodiment, the temperature change composition can be applied to an exterior surface of a bath tissue product 50. As shown, the bath tissue product 50 contains a spirally wound product containing individual tissue sheets 52 separated by perforation lines 54. The tissue sheets can include a first exterior surface 56 and a second exterior surface 58. Each tissue sheet may contain a single ply product or a multi-ply product. In accordance with the present disclosure, the temperature change composition may be present on the first exterior surface 56, on the second exterior surface 58, or on both exterior surfaces.

Figure 4:
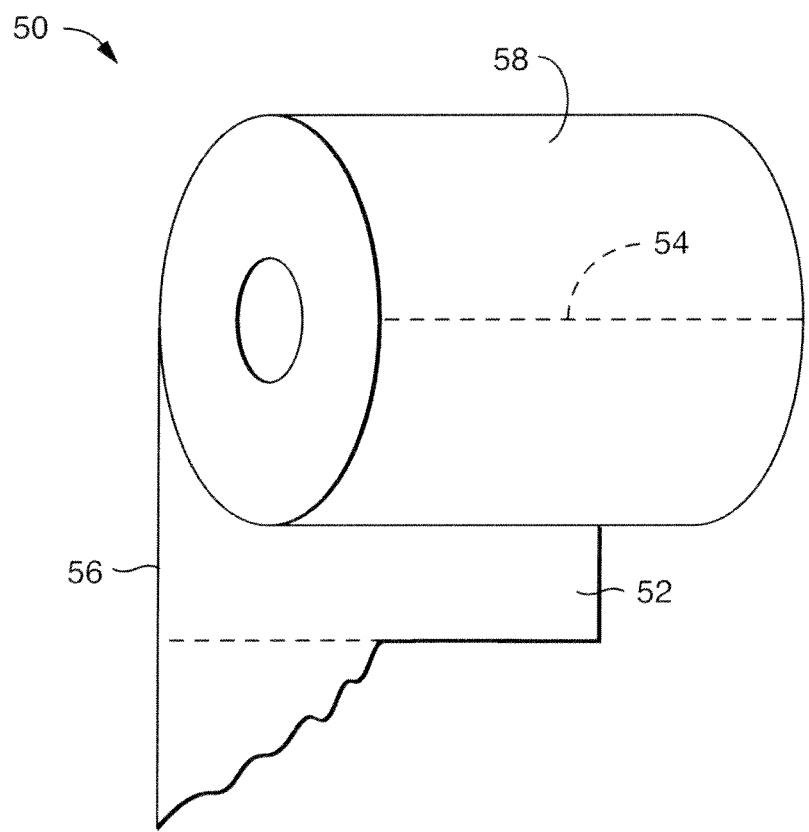
FIG. 4 is a perspective view of one embodiment of a spirally wound bath tissue product made in accordance with the present disclosure.

Applying the temperature change composition to a bath tissue product as shown in FIG. 4 may provide various unexpected benefits and advantages. For example, the temperature change composition may provide a cooling sensation that actually makes the bath tissue sheet evoke a sensation of wetness to the user. The sense of wetness can lead to a perception of improved cleaning.

When applied to a bath tissue as shown in FIG. 4, the temperature change composition may contain a moisturizer, as described above, so as to provide further benefits to the user.

When hydrophobic phase change components are used, it may be advantageous to utilize methods to reduce the impact of any hydrophobicity that may develop due to the presence of the hydrophobic phase change components. A variety of methods are known in the art for reducing hydrophobicity of tissue sheets containing hydrophobic additives. For example, hydrophilic surfactants having an HLB of greater than 4 may be combined into the temperature change composition as taught in U.S. Pat. No. 6,428,794 B1, "Lotion composition for treating tissue paper". Other exemplary means for reducing the hydrophobicity of the tissue sheet include but are not limited to those taught in U.S. Pat. No. 6,949,167 B2, US20050274470 A1, U.S. Pat. No. 6,896,766 B2, and U.S. Pat. No. 7,008,507 B2 incorporated by reference herein.

EXAMPLES

Examples 1-13

The present disclosure may be better understood with reference to the following examples.

The following is a list of 13 temperature change compositions suitably containing a phase change component and a non-interfering molecular scaffold. Comparative Example 1 does not include a non-interfering molecular scaffold.

For the phase change component, stearyl heptanoate is used. Stearyl heptanoate has a melting point of 23-27° C. and a latent heat of fusion of around 174 J/g. Stearyl heptanoate is an ester of stearyl alcohol and heptanoic acid (enanthic acid). It is prepared from stearyl alcohol, which may be derived from sperm whale oil or from vegetable sources. Stearyl heptanoate melts on the skin rapidly between 23-27° C. causing cooling of the skin. For the non-interfering molecular scaffold, a variety of different crystalline diluents are used.

TABLE 1

Example Compositions

| Composition | Wt. % Phase change component | Non-interfering molecular scaffold | Wt. % Non-interfering molecular scaffold |
|---|---|---|---|
| Example 1 | 90 | Lauric Acid | 10 |
| Example 2 | 90 | Lauryl Alcohol | 10 |
| Example 3 | 90 | Palmitic Acid | 10 |
| Example 4 | 90 | Cetyl Alcohol | 10 |
| Example 5 | 90 | Cetearyl Alcohol | 10 |
| Example 6 | 90 | Stearyl Alcohol | 10 |
| Example 7 | 90 | Stearic Acid | 10 |
| Example 8 | 90 | Behenyl Alcohol | 10 |
| Example 9 | 90 | Behenic Acid | 10 |
| Example 10 | 90 | Dodecylhexadecanol | 10 |
| Example 11 | 90 | C20-40 Alcohols | 10 |
| Example 12 | 90 | Behentrimonium Methosulfate (and) Cetearyl Alcohol | 10 |
| Example 13 | 80 | Stearyl Alcohol | 20 |
| Comparative Example 1 | 100 | N/A | 0 |

The latent heat of fusion and melting points of various compositions were determined by differential scanning calorimetry. The samples were analyzed on a TA Instruments DSC 2920 Modulated DSC (Standard Cell) using the following experimental procedure: Approximately 5 mg of the respective material was weighed to the nearest 0.1 mg. Samples were run in the temperature interval from −50° C. to 100° C. with a heating/cooling rate of 10° C./min in an inert gas ($N_2$) atmosphere. The heat of fusion ($\Delta H_f$) was computed from the integral under the respective melting peak (melting point), with the reported results being the average value from 3 heating/cooling cycles. Values calculated for the examples are illustrated in Table 2.

TABLE 2

Enthalpy Calculations

| Composition | Peak Melt Temp. ° C. | End of Melt ° C. | $\Delta H_f$ J/g | % Cooling of Pure |
|---|---|---|---|---|
| Example 1 | 27.35 | 65.25 | 166.3 | 93.9 |
| Example 2 | 26.21 | 38.7 | 173.8 | 98.14 |
| Example 3 | 28.08 | 46.04 | 148.8 | 84.02 |
| Example 4 | 26.69 | 41.12 | 175.5 | 99.10 |
| Example 5 | 28.61 | 47.58 | 165.8 | 93.62 |
| Example 6 | 28.35 | 54.79 | 182.6 | 103.22 |
| Example 7 | 29.85 | 46.72 | 150.6 | 85.04 |
| Example 8 | 28.99 | 65.59 | 174.7 | 98.64 |
| Example 9 | 29.6 | 65.25 | 137.3 | 77.53 |
| Example 10 | 27.17 | 42.78 | 163.4 | 92.26 |
| Example 11 | 27.53 | 40.89 | 161.3 | 91.08 |
| Example 12 | 26.55 | 41.41 | 175.5 | 99.1 |
| Example 13 | 26.42 | 60.96 | 193.6 | 109.32 |
| Comparative Example 1 | 28.14 | 45.69 | 177.1 | 100.0 |

Examples 1-13 illustrate that by using a crystalline diluent material, the temperature change composition still provides enough enthalpy to provide a cooling sensation. If the concentration of phase change material was directly proportional to the cooling ability (enthalpy), then an enthalpy of 159.39 J/g would be expected from a 10% reduction in the full enthalpy of 100% of the phase change material. As is evidenced by Table 2, several exemplary compositions retained a high percentage of enthalpy of 100% stearyl heptanoate while reducing the overall loading of the phase change material by 10-20%. A particularly well performing composition included stearyl heptanoate as the phase change material and stearyl alcohol as the crystalline diluent.

Not to be held to any one theory, but it is believed that the self assembling crystalline structure of the diluent materials provides non-interfering molecular scaffolding for the phase change material. Thus, the phase change material aggregates within and around the non-interfering molecular scaffolding such that the crystal size of the phase change material is sufficient to provide an equivalent cooling sensation compared to the pure phase change material.

Example 14

Example 14 demonstrates application of the temperature change composition to a tissue basesheet to produce a facial tissue product having a cooling perception. A three-ply creped tissue sheet having a finished basis weight of 44 gsm consisting of 65 percent hardwood and 35 percent softwood fibers was used. Each ply was made from a stratified fiber furnish including two outer layers and a middle layer. A composition including 70 wt. % stearyl heptanoate, 25 wt. % stearyl alcohol, and 5 wt. % polyethylene was made in the lab, coated on tissues and put into a modified repetitive nose wipe and adaptable methodology panel. Results from this study showed improved aesthetics, lower TEWL, lower redness scores and lower dropout rates data from similar tests with stearyl heptanoate at 100% levels or at a 90:10 weight ratio with cosmetic wax. The tissue sheet was also found to give a pronounced cooling sensation when held in hand or against the face.

Example 15

Example 15 illustrates an alternative embodiment of the temperature change composition containing 90 wt. % stearyl heptanoate and 10 wt. % polystyrene-poly(ethylene-butylene-styrene)-polystyrene (S-EB/S-S) triblock copolymers (Kraton RP-6936).

Example 15 was made in the laboratory by heating the stearyl heptanoate to 100-120° C. The polymer was added with homogenization (7,000 rpm) for 20 minutes or until completely wetted and dispersed. Once the polymer solution was completely clear and homogenous, the mixture was allowed to cool to room temperature. The off-white to white gel was pliable and melted at body temperature. Upon melting, a high degree of cooling was experienced from the temperature change composition by human subjects touching the gel. The Example 15 composition was coated on tissues and put into a modified repetitive nose wipe and adaptable methodology panel. Results from this study showed improved aesthetics, lower TEWL, lower redness scores and lower dropout rates data from similar tests with stearyl heptanoate at 100% levels or at a 90:10 weight ratio with cosmetic wax. The tissue sheet was also found to give a pronounced cooling sensation when held in hand or against the face.

These and other modifications and variations to the appended claims may be practiced by those of ordinary skill in the art, without departing from the spirit and scope of the appended claims. In addition, it should be understood that aspects of the various embodiments may be interchanged both in whole and in part. Furthermore, those of ordinary skill in the art will appreciate that the foregoing description is by way of example only, and is not intended to limit the appended claims.

What is claimed:

1. A dry substrate comprising:
   a first tissue web comprised of fibers, the web including a first side and a second side; and
   a temperature change composition present on at least the first side of the tissue web, the temperature change composition comprising:
   a phase change component that undergoes a phase change at a temperature from about 20° C. to about 35° C., the phase change component having a heat of fusion of at least about 100 J/g and being present on the tissue web such that the tissue web has a heat absorption factor of at least about 500 $J/m^2$, the phase change component present in an amount between about 1% by weight of the temperature change composition and about 99.9% by weight of the temperature change composition,
   a non-interfering molecular scaffold present in an amount between about 1% by weight of the temperature change composition and about 50% by weight of the temperature change composition,
   the non-interfering molecular scaffold comprising an ingredient that combines with the phase change component into a homogeneous mixture that (a) maintains a gel-like consistency at 40 degrees Celsius, and (b) retains at least 75% of the enthalpy of the phase change component in a pure form,
   wherein the non-interfering molecular scaffold comprises a crystalline diluent selected from fatty alcohols and fatty acids, the fatty alcohols and fatty acids having a chain length from 6 to about 50 carbon atoms, and
   wherein the non-interfering molecular scaffold comprises a polymer selected from polyethylene, $C_{8-22}$ alkyl acrylates/methacrylic acid crosspolymer, $C_{8-22}$ alkyl acrylate/butyl dimethicone methacrylate copolymer, polystyrene-poly(ethylene-propylene) diblock copolymers, polystyrene-poly(ethylene-butylene-styrene)-polystyrene (S-EB/S-S) triblock copolymers, maleic anhydride-grafted polystyrene-polyethylene-butylene)-polystyrene triblock copolymers, maleic anhydride-grafted polystyrene-polyethylene-butylene-styrene)-polystyrene triblock copolymers, polystyrene-polybutadiene-poly(styrene-butadiene)-polybutadiene block copolymers, hydrogenated radial block copolymers, and mixtures thereof.

2. The dry substrate of claim 1 wherein the fatty alcohols and fatty acids have a chain length from 10 to about 30 carbon atoms.

3. The dry substrate of claim 1 wherein the phase change component is present in an amount between about 20% by weight of the temperature change composition and about 95% by weight of the temperature change composition.

4. The dry substrate of claim 1 wherein the phase change component is present in an amount between about 50% by weight of the temperature change composition and about 90% by weight of the temperature change composition.

5. The dry substrate of claim 1 wherein the non-interfering molecular scaffold is present in an amount between about 2% by weight of the temperature change composition and about 45% by weight of the temperature change composition.

6. The dry substrate of claim 1 wherein the non-interfering molecular scaffold is present in an amount between about 5% by weight of the temperature change composition and about 40% by weight of the temperature change composition.

7. The dry substrate of claim 1 wherein the phase change component is oil soluble and hydrophobic.

8. The dry substrate of claim 1 wherein the phase change component is selected from tricaprin, paraffin, nonadecane, octadecane, stearyl heptanoate, lauryl lactate, lauryl alcohol, capric acid, caprylic acid, cetyl babassuate, mangifera indica (mango) seed butter, theobroma cacao (cocoa) seed butter, butyrospermum parkii butter, Di-$C_{12-15}$ Alkyl Fumarate, stearyl caprylate, cetyl lactate, cetyl acetate, $C_{24-28}$ alkyl methicone, glyceryl dilaurate, stearamidopropyl PG-dimonium chloride phosphate, jojoba esters, and combinations thereof.

9. The dry substrate of claim 1 wherein the phase change component has a heat of fusion of about 174 J/g.

10. The dry substrate of claim 1 further comprising a lotion composition, the lotion composition being located on an exterior surface of the tissue web.

11. The dry substrate of claim 1 wherein the temperature change composition is present on the tissue web in an amount from about 4 gsm to about 40 gsm.

12. The dry substrate of claim 1 wherein the phase change component contains a hydrocarbon, a wax, an oil, a natural butter, a fatty acid, a fatty acid ester, a dibasic acid, a dibasic ester, a 1-halide, a primary alcohol, an aromatic compound, an anhydride, an ethylene carbonate, a polyhydric alcohol, or mixtures thereof.

13. The dry substrate of claim 1 wherein the phase change component comprises stearyl heptanoate and the non-interfering molecular scaffold comprises stearyl alcohol.

14. The dry substrate of claim 13 wherein the non-interfering molecular scaffold further comprises polyethylene.

15. The dry substrate of claim 1 wherein the non-interfering molecular scaffold is selected from crystalline diluents, polymers, block copolymers, and combinations thereof.

* * * * *